United States Patent
Behrendt et al.

(10) Patent No.: US 12,181,478 B2
(45) Date of Patent: Dec. 31, 2024

(54) LIGHT-EMITTING MARKER PARTICLES

(71) Applicant: Sumitomo Chemical Company Limited, Tokyo (JP)

(72) Inventors: Jonathan Behrendt, Bedford (GB); Melanie O'Sullivan, Godmanchester (GB)

(73) Assignee: Sumitomo Chemical Company Limited, Tokyo (JP)

( * ) Notice: Subject to any disclaimer, the term of this patent is extended or adjusted under 35 U.S.C. 154(b) by 926 days.

(21) Appl. No.: 17/278,245

(22) PCT Filed: Sep. 9, 2019

(86) PCT No.: PCT/GB2019/052511
§ 371 (c)(1),
(2) Date: Mar. 19, 2021

(87) PCT Pub. No.: WO2020/058668
PCT Pub. Date: Mar. 26, 2020

(65) Prior Publication Data
US 2021/0356471 A1    Nov. 18, 2021

(30) Foreign Application Priority Data

Sep. 20, 2018  (GB) .................................. 1815325
Aug. 8, 2019   (GB) .................................. 1911365

(51) Int. Cl.
*G01N 33/58*    (2006.01)
*C09K 11/02*    (2006.01)
(Continued)

(52) U.S. Cl.
CPC ............ *G01N 33/582* (2013.01); *C09K 11/02* (2013.01); *C09K 11/025* (2013.01); *C09K 11/06* (2013.01);
(Continued)

(58) Field of Classification Search
CPC ....... C09K 11/02; C09K 11/025; C09K 11/06; C09K 2211/14; G01N 33/533; G01N 33/54346; G01N 33/582; G01N 33/587
See application file for complete search history.

(56) References Cited

U.S. PATENT DOCUMENTS 9,810,693 B2   11/2017  Chiu et al.
2010/0209946 A1  8/2010  Jing et al.
(Continued)

FOREIGN PATENT DOCUMENTS

EP    2 833 144 A1    2/2015
EP    3 012 632 A1    4/2016
(Continued)

OTHER PUBLICATIONS

Japanese Office Action dated Aug. 2, 2023, in connection with Japanese Application No. 2021-515076.
(Continued)

*Primary Examiner* — Jennifer Wecker
(74) *Attorney, Agent, or Firm* — Wolf, Greenfield & Sacks, P.C.

(57) ABSTRACT

A light-emitting marker particle having a light-emitting particle core containing a light-emitting material and first and second surface groups bound to the light-emitting particle core. The first surface group contains a polar group and is an inert group which does not bind to a biomolecule. The second surface group contains a biomolecule binding group.

20 Claims, 7 Drawing Sheets

(51) Int. Cl.
  *C09K 11/06* (2006.01)
  *G01N 33/533* (2006.01)
(52) U.S. Cl.
  CPC ........ *G01N 33/533* (2013.01); *C09K 2211/14* (2013.01)

(56) References Cited

U.S. PATENT DOCUMENTS

| | | | |
|---|---|---|---|
| 2011/0226991 A1* | 9/2011 | Treadway | B82Y 30/00 977/773 |
| 2011/0236957 A1* | 9/2011 | Weng | B82Y 15/00 435/235.1 |
| 2012/0219496 A1 | 8/2012 | Tsourkas et al. | |
| 2015/0314019 A1 | 11/2015 | Sokolov et al. | |
| 2016/0250612 A1* | 9/2016 | Oldenburg | B01J 13/20 428/404 |

FOREIGN PATENT DOCUMENTS

| | | | | |
|---|---|---|---|---|
| GB | 2554666 | A | 4/2018 | |
| GB | 2577292 | A * | 3/2020 | ........... C09K 11/025 |
| JP | 2009-236848 | A | 10/2009 | |
| JP | 2011-516885 | A | 5/2011 | |
| JP | 2012-242394 | A | 12/2012 | |
| JP | WO2013/146694 | | 12/2015 | |
| JP | 2016-194529 | A | 11/2016 | |
| JP | WO2014/203614 | | 2/2017 | |
| JP | WO2015/146938 | | 4/2017 | |
| JP | 2017-150867 | A | 8/2017 | |
| JP | 2022-502534 | A | 1/2022 | |
| WO | WO 2009/126259 | A1 | 10/2009 | |
| WO | WO 2011/057295 | A2 | 5/2011 | |
| WO | WO 2011/109214 | A2 | 9/2011 | |
| WO | WO 2015/146938 | A1 | 10/2015 | |
| WO | WO 2017/178882 | A1 | 10/2017 | |
| WO | WO 2018/060722 | A1 | 4/2018 | |
| WO | WO 2020/060937 | A1 | 3/2020 | |

OTHER PUBLICATIONS

Auger et al., A comparative study of non-covalent encapsulation methods of organic dyes into silica nanoparticles. Nanoscale Research Letters. 2011. 6(328). 12 Pages.

Behrendt et al., Hybrid inorganic-organic composite nanoparticles from crosslinkable polyfluorenes. Journal of Materials Chemistry C. Feb. 8, 2013;1(3297). 8 Pages. DOI: 10.1039/c3tc30266k.

Carmen-Estevez et al., Highly Fluorescent Dye-Doped Silica Nanoparticles Increase Flow Cytometry Sensitivity for Cancer Cell Monitoring. Nano Research.2009. 2:448-61.

Geng et al., A general approach to prepare conjugated polymer dot embedded silica nanoparticles with a SiO2@CP@SiO2 structure for targeted HER2-positive cellular imaging. Nanoscale. May 9, 2013;5:8593-8601.

Geng et al., Micelle/Silica Co-protected Conjugated Polymer Nanoparticles for Two-Photon Excited Brain Vascular Imaging. Chem. Mater. Feb. 18, 2014;26(5):1874-1880.

Van Blaaderen et al., Synthesis and Characterization of Colloidal Dispersions of Fluorescent, Monodisperse Silica Spheres. Langmuir. Feb. 7, 1992;8:2921-31.

International Search Report and Written Opinion mailed Nov. 6, 2019 in connection with International Application No. PCT/GB2019/052511.

Combined Search and Examination Report dated Mar. 18, 2019 in connection with GB Application No. 1815325.4.

Combined Search and Examination Report dated Feb. 6, 2020 in connection with GB Application No. 1911365.3.

GB 1815325.4, Mar. 18, 2019, Combined Search and Examination Report.

GB 1911365.3, Feb. 6, 2020, Combined Search and Examination Report.

PCT/GB2019/052511, Nov. 6, 2019, International Search Report and Written Opinion.

\* cited by examiner

LIGHT-EMITTING MARKER PARTICLES

RELATED APPLICATIONS

This Application is a national stage filing under 35 U.S.C. § 371 of international PCT application no. PCT/GB2019/052511, filed Sep. 9, 2019, which claims priority to United Kingdom patent application no. GB 1911365.3, filed Aug. 8, 2019, and United Kingdom patent application no. GB 1815325.4, filed Sep. 20, 2018, each of which is incorporated herein by reference in its entirety.

BACKGROUND

In some embodiments, the present disclosure provides light-emitting marker particles, optionally light-emitting marker nanoparticles, for use as markers in biosensor applications.

Nanoparticles of silica and a light-emitting material have been disclosed as labelling or detection reagents.

WO 2018/060722 discloses composite particles comprising a mixture of silica and a light-emitting polymer having polar groups.

Estevez, M-C. et al. 'Highly Fluorescent Dye-Doped Silica Nanoparticles Increase Flow Cytometry Sensitivity for Cancer Cell Monitoring' *Nano. Res.* 2009, 2, 448-461 discloses dye-doped silica nanoparticles functionalised with polyethylene glycol.

US 2010/209946 discloses silica nanoparticles functionalised with water dispersible groups, shielding groups and biomolecule binding groups.

Nanoscale, 2013, vol. 5, pp 8593-8601, Geng et al. describes silica-conjugated polymer (CP) nanoparticles wherein the LEP has pendant non-polar alkyl side chains and where the nanoparticles have a "$SiO_2@CP@SiO_2$" structure.

Behrendt et al. *J. Mater. Chem.*, 2013, vol. 1, pp 3297-3304, describes silica-LEP nanoparticles where the LEP is covalently bound to the silica. The light emitting polymer has alkoxysilane groups pendant from the polymer backbone which react with the silica monomer during formation of the nanoparticles.

Nanoscale Res. Lett., 2011, vol. 6, p 328 discloses entrapment of a small molecule in a silica matrix.

Langmuir, 1992, vol. 8, pp 2921-2931 discloses coupling of a dye to a silane coupling agent which is then incorporated into a silica sphere.

Chem. Mater., 2014, vol. 26, pp 1874-1880, Geng et al. discloses poly(9,9-dihexylfluorene-alt-2,1,3-benzothiadiazole) (PFBT) loaded nanoparticles.

SUMMARY

A summary of aspects of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects and/or a combination of aspects that may not be set forth.

It is desirable for light-emitting particles configured to bind to a biomolecule to form a colloid which is stable, and in particular which does not aggregate, when in use and/or when in storage. The present inventors have found that maintaining stability of such colloids is particularly problematic in aqueous solutions commonly used in biological assays such as aqueous buffer solutions.

The present inventors have found that a stable colloid containing light-emitting marker nanoparticles may be formed, while maintaining the ability of the light emitting marker particles to bind to biomolecules, from particles having polar surface groups with biomolecule binding groups and surface groups without biomolecule binding groups.

Accordingly, in some embodiments there is provided a light-emitting marker particle having a light-emitting particle core containing a light-emitting material, and first and second surface groups bound to the light-emitting particle core. The first surface group contains a polar group and is inert. The second surface group contains a biomolecule binding group.

In some embodiments, the first surface group: second surface group molar ratio is greater than 90:10.

The aforementioned problem of aggregation may be exacerbated for light-emitting particles in which the light-emitting material is a polymer. However, the present inventors have found that good stability may be achieved using surface groups as described herein for a light-emitting core containing a light-emitting polymer.

Accordingly, in some embodiments the light-emitting material is a light-emitting polymer.

In some embodiments, the nanoparticle core contains an inorganic matrix. The inorganic matrix may be an inorganic oxide, optionally silica.

The present inventors have found that marker particles having surface groups with and without biomolecule binding groups may be formed such that the ratio of biomolecule binding groups to non-biomolecule binding groups may be controlled. This ratio may be selected to balance the colloidal stability of the particles with the particles' biomolecule binding capacity.

Accordingly, in some embodiments there is provided a method of forming a light-emitting marker particle in which a light-emitting particle core having a plurality of a first reactive group bound to a surface thereof is reacted with first and second reactive compounds to form the first and second surface groups, respectively, or precursors of the first and second surface groups which may undergo one or more further reactions to form the first and second surface groups.

The particles may be dispersed in a liquid, e.g. for use in an assay.

Accordingly, in some embodiments there is provided a colloidal suspension comprising the particles suspended in a liquid.

The particles may be used for marking a biomolecule, e.g. to track or detect the biomolecule. Accordingly, in some embodiments there is provided a method of marking a biomolecule comprising the step of binding the biomolecule to the particle.

In some embodiments there is provided an assay method for a target analyte comprising contacting a sample with light-emitting marker particles as described herein and determining any binding of the target analyte to the light-emitting marker.

Optionally, the sample contacted with the light-emitting marker particles is analysed by flow cytometry.

Optionally, an amount of target analyte bound to the light-emitting marker particles is determined.

Optionally, the sample comprises a mixture of cells and one or more different types of target cells bound to the light-emitting marker are identified and/or quantified

DESCRIPTION OF THE DRAWINGS

The present disclosure is described in conjunction with the appended figures. It is emphasized that, in accordance with the standard practice in the industry, various features are not drawn to scale. In fact, the dimensions of the various features may be arbitrarily increased or reduced for clarity of discussion.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

Figure 1:
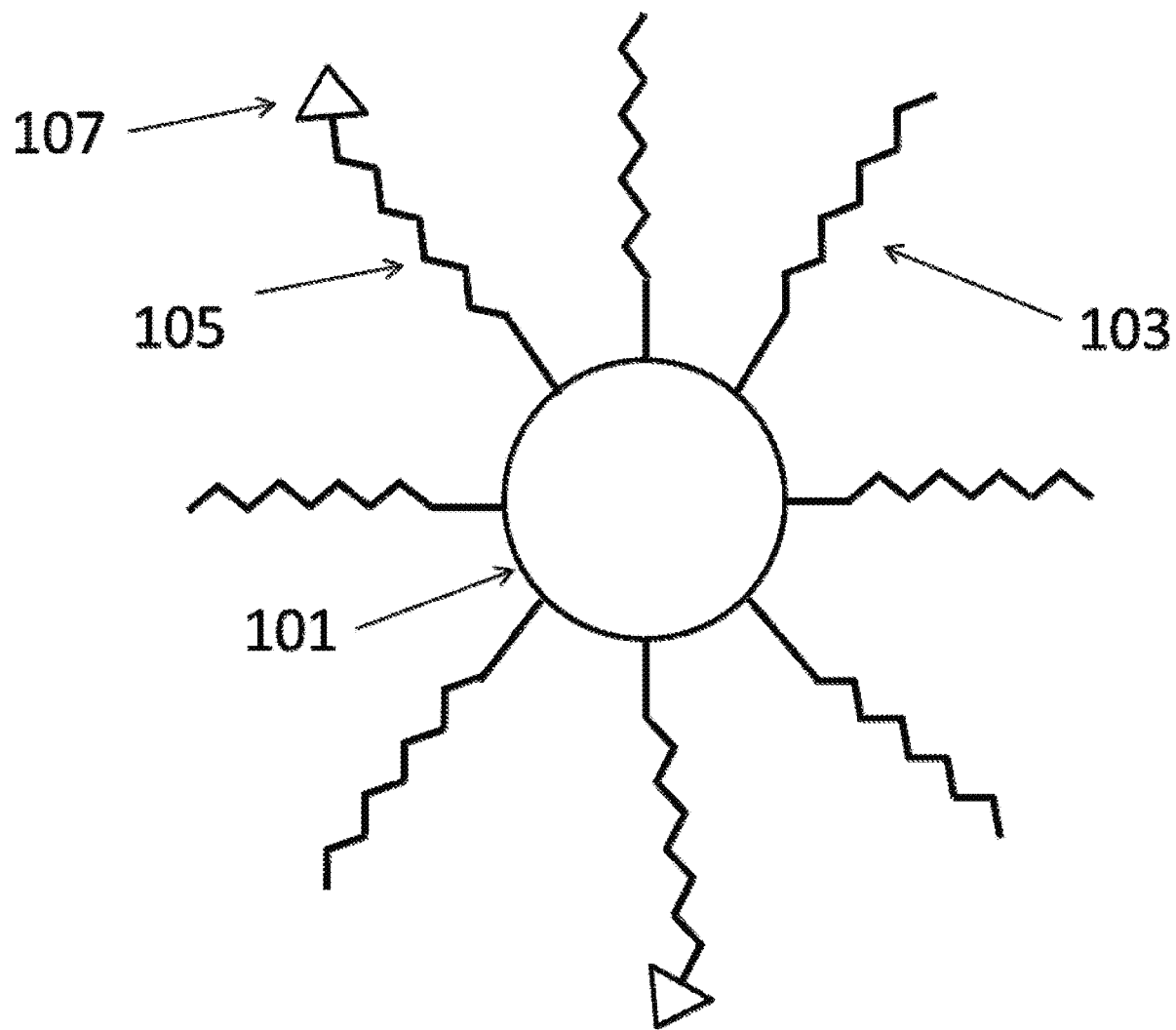
Figure 2:
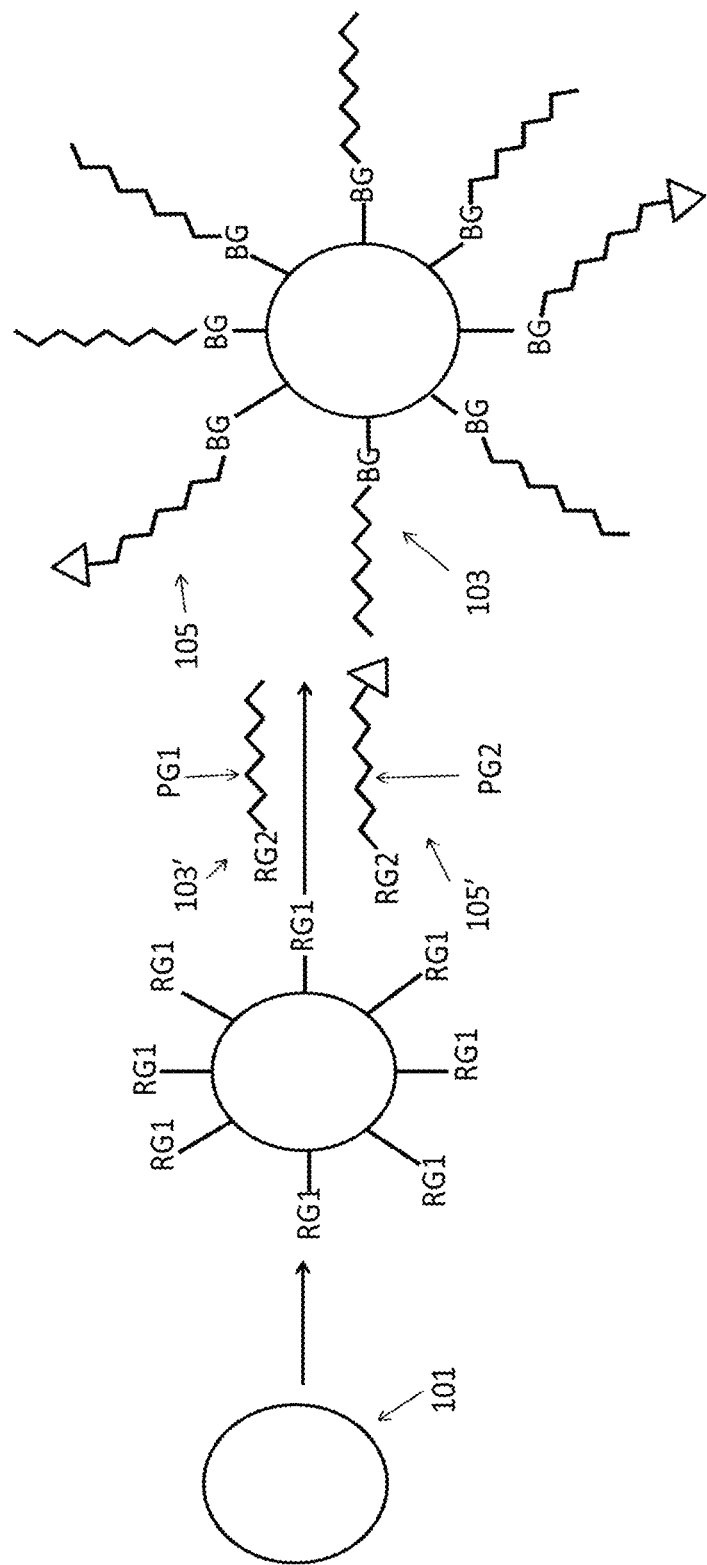
Figure 3:
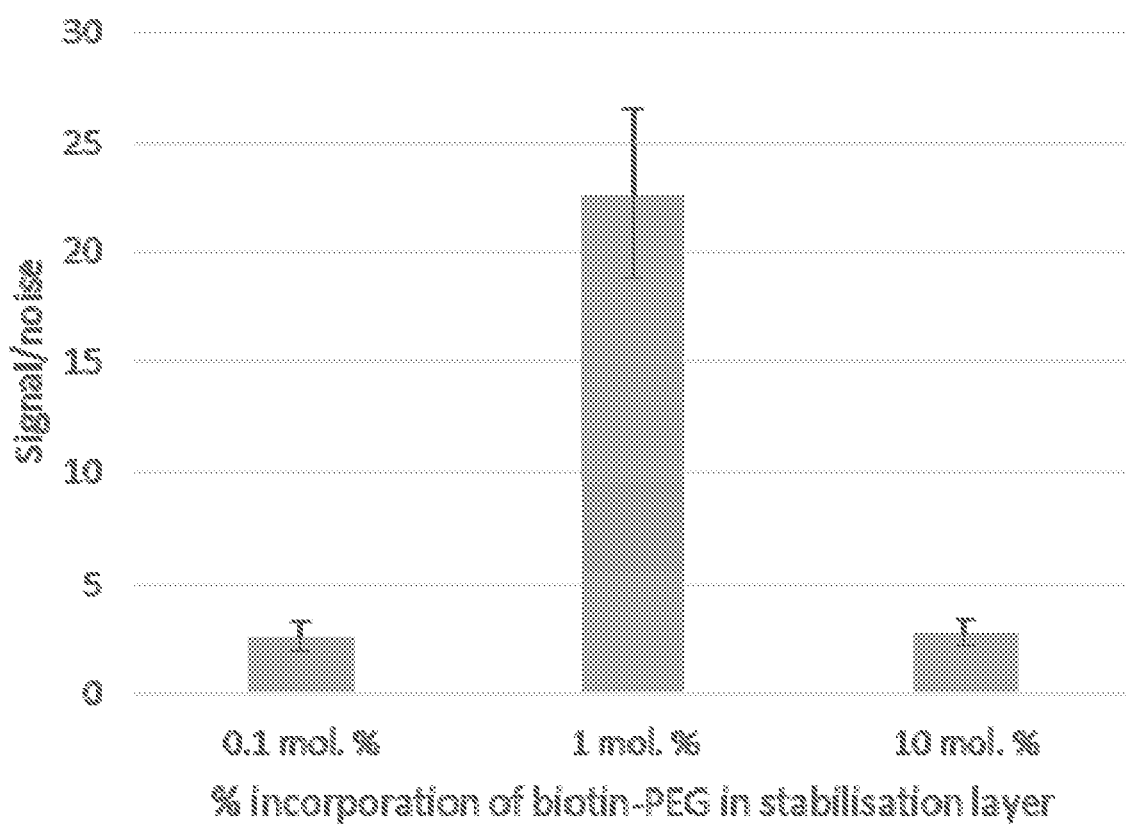

The invention will now be described in more detail with reference to the drawings wherein:

FIG. 1 is a schematic illustration of a nanoparticle according to some embodiments;

FIG. 2 is schematic illustration of a method of forming a nanoparticle according to some embodiments;

FIG. 3 is a graph of signal-to-noise ratio for light-emitting nanoparticles in which 0.1. 1 and 10 mol % of the nanoparticle surface groups contain a biotin binding group.

Figure 4:
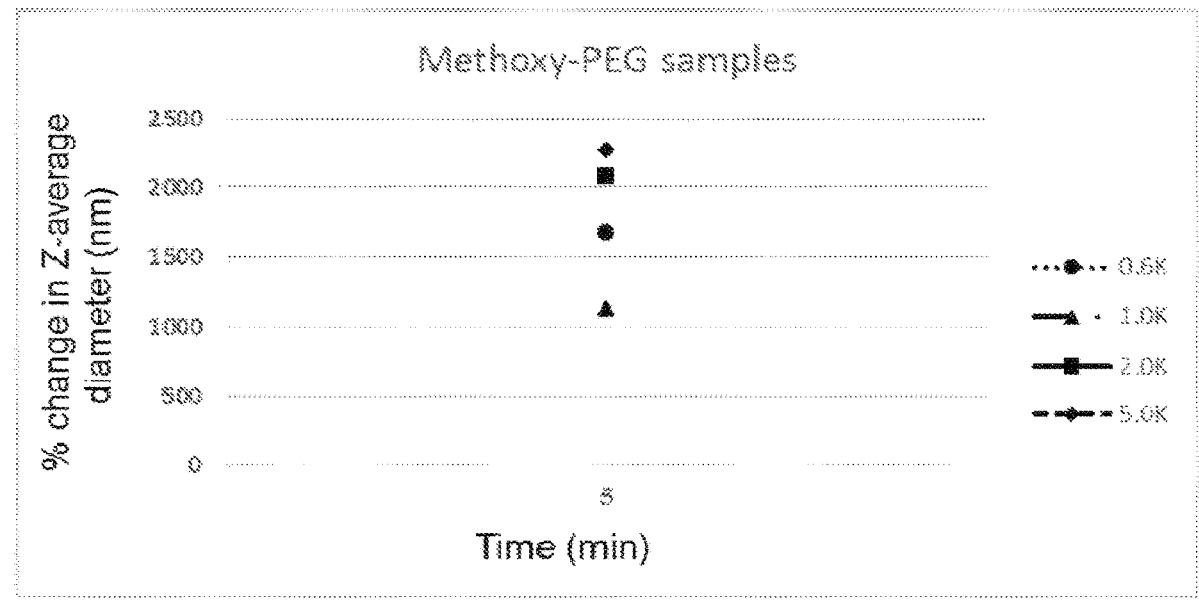
Figure 5:
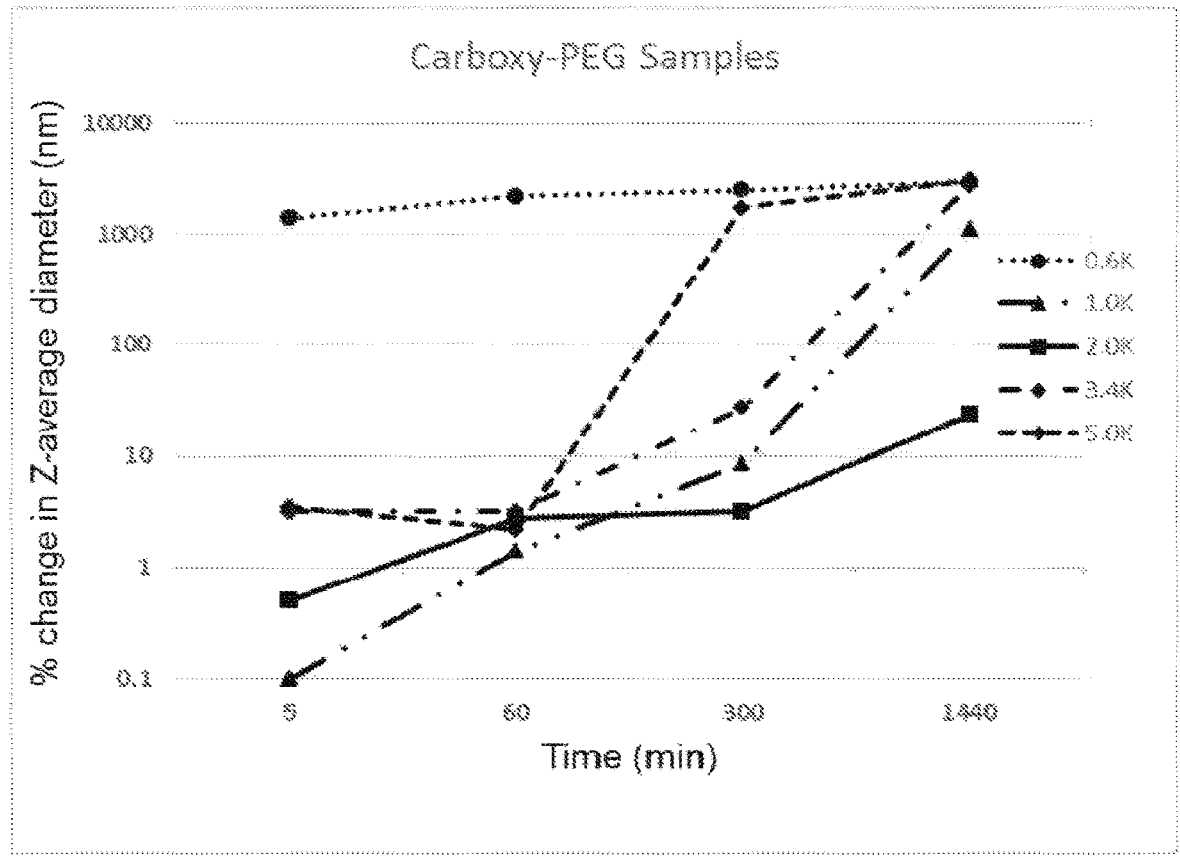
Figure 6:
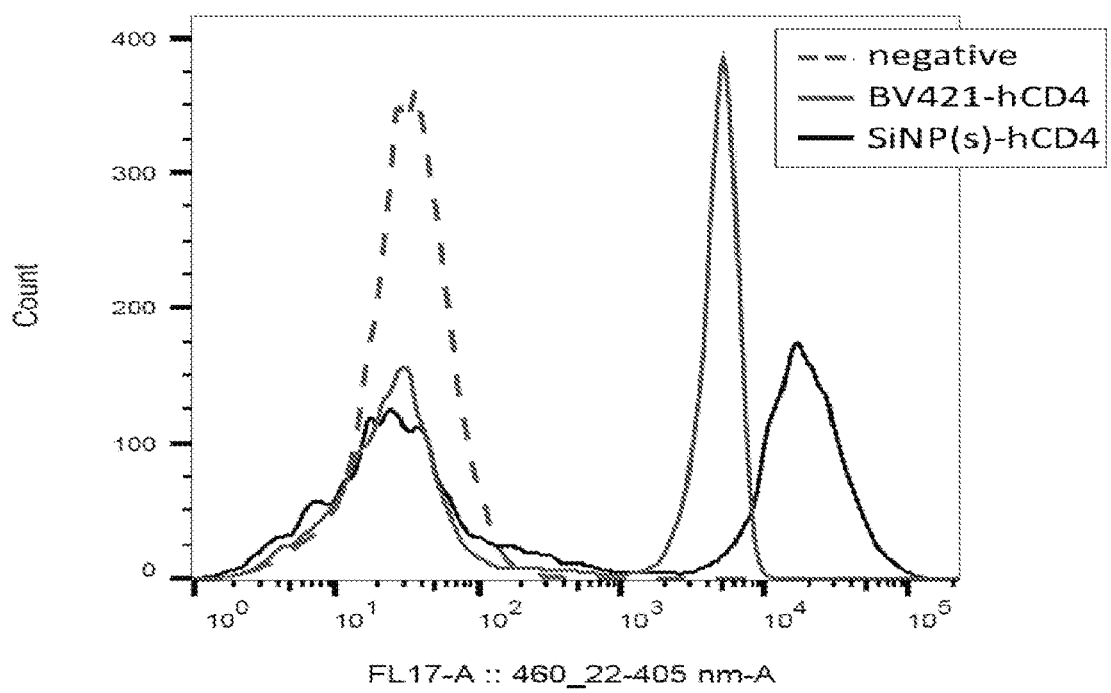
Figure 7:
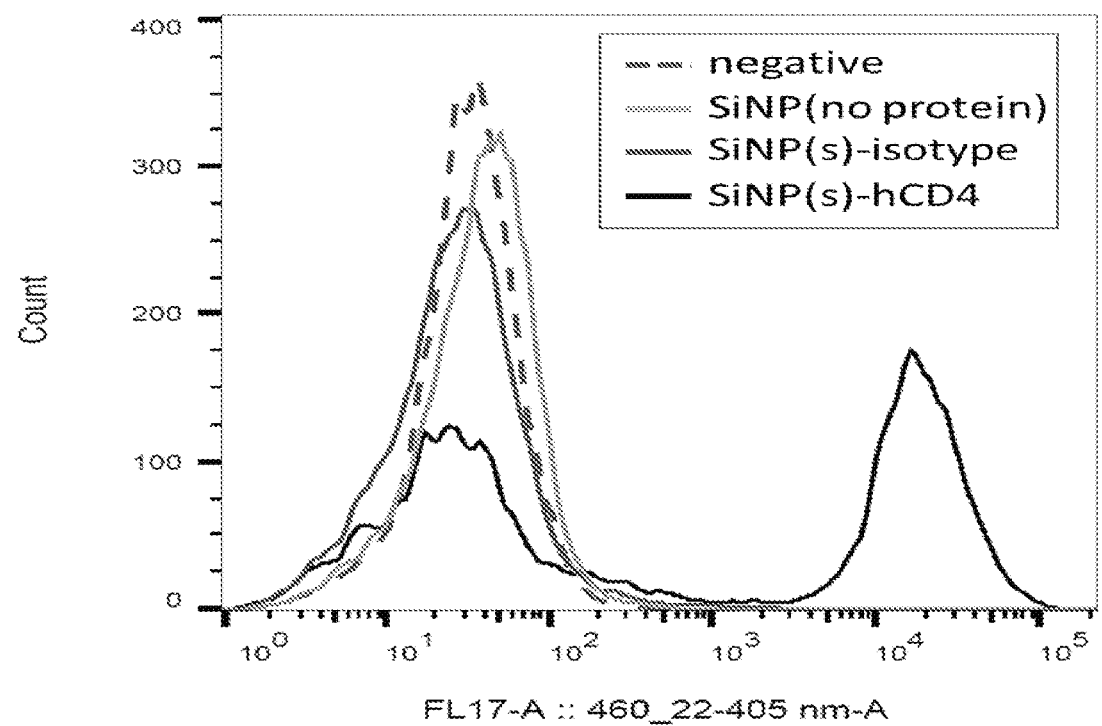
Figure 8:
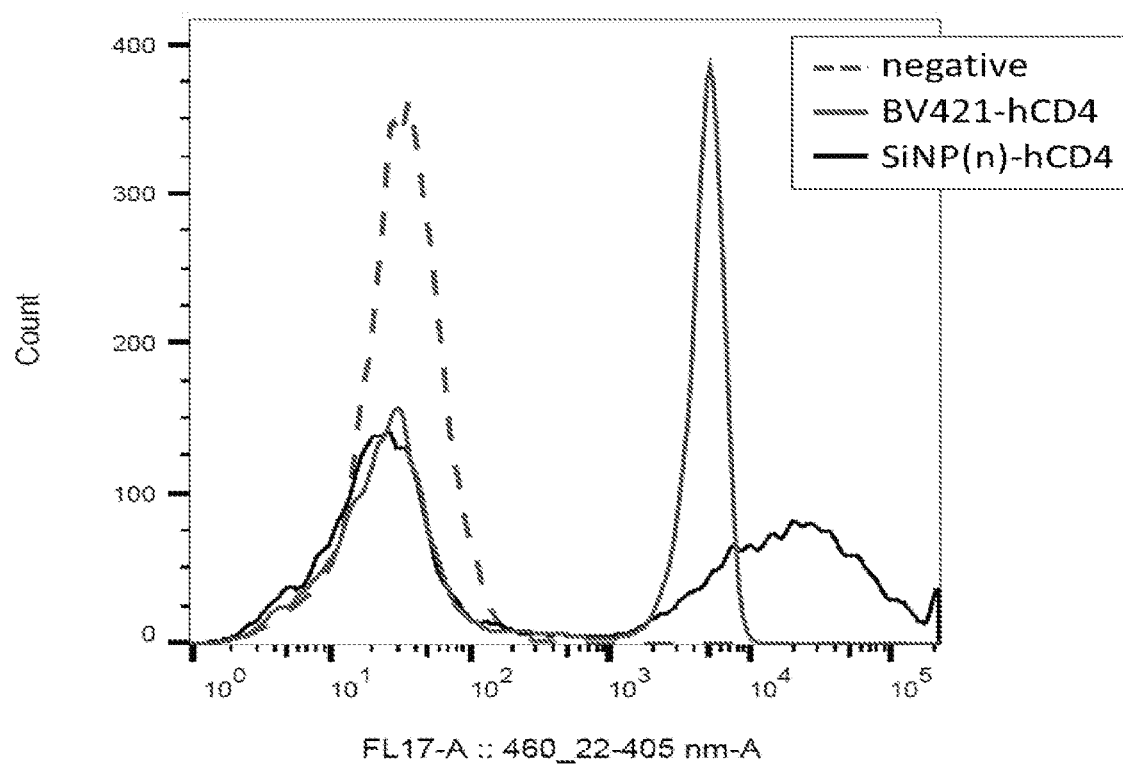
Figure 9:
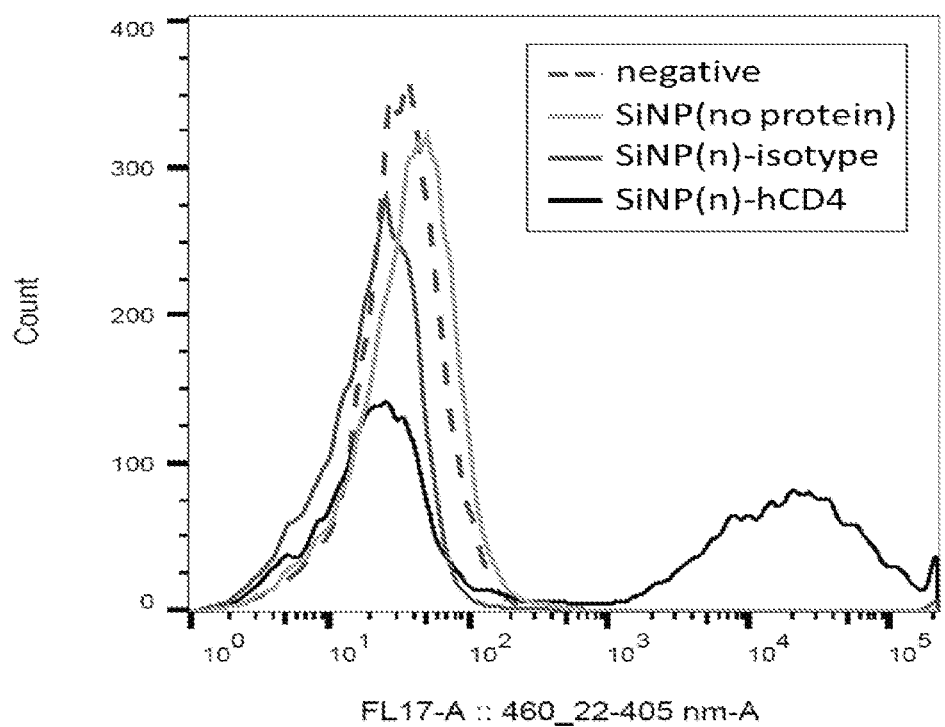
Figure 10:
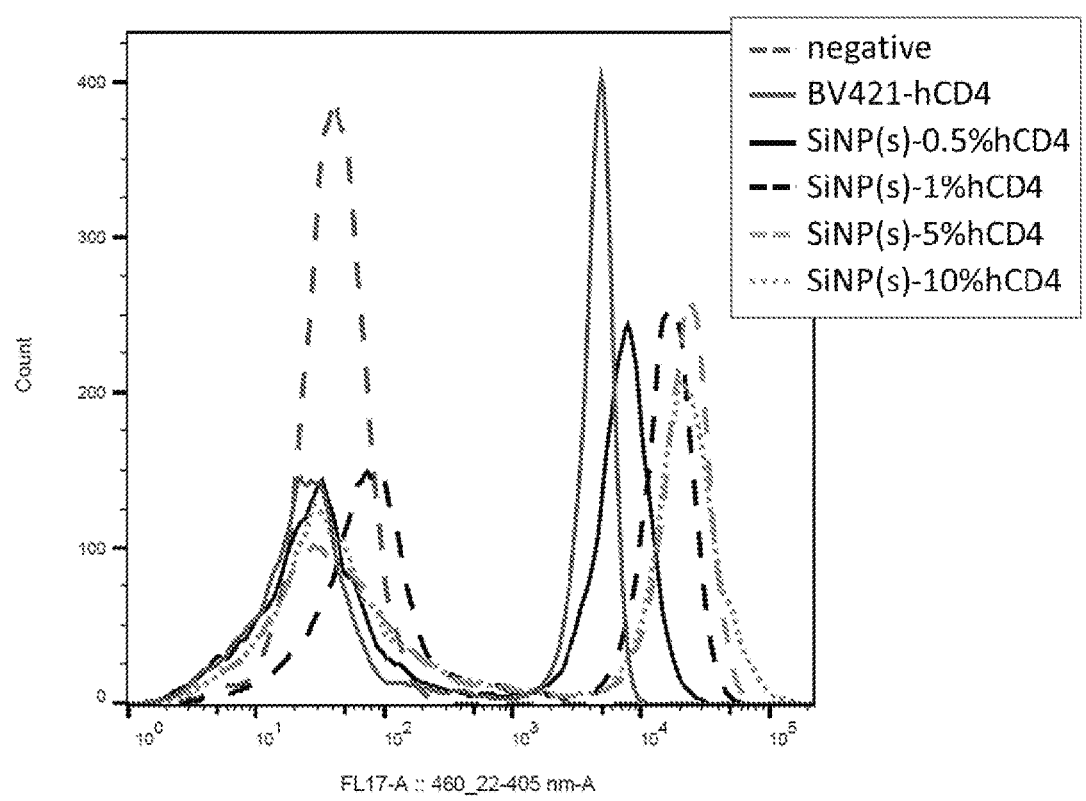

FIG. 4 is a graph of percentage change in Z-average diameter vs time of nanoparticles having a methoxy-terminated surface group dispersed in a buffer solution;

FIG. 5 is a graph of percentage change in Z-average diameter vs time of nanoparticles having a carboxy-terminated surface group dispersed in a buffer solution;

FIG. 6 is a staining index chart for Cyto-Trol cells stained with a biotinylated dissolved light-emitting polymer marker according to an embodiment of the present disclosure conjugated through streptavidin to anti-human CD4 antibody; and a comparative light-emitting nanoparticle conjugated to the same antibody;

FIG. 7 is a staining index chart for Cyto-Trol cells stained with the streptavidin-conjugated nanoparticle of FIG. 6; a light-emitting nanoparticle conjugated to an isotype; and a light-emitting nanoparticle which is not conjugated to streptavidin;

FIG. 8 is a staining index chart for Cyto-Trol cells stained with a biotinylated nanoparticle according to an embodiment of the present disclosure conjugated through neutravidin to anti-human CD4 antibody; and a comparative dissolved light-emitting polymer marker conjugated to the same antibody;

FIG. 9 is a staining index chart for Cyto-Trol cells stained with the neutravidin-conjugated nanoparticle of FIG. 8; a light-emitting nanoparticle conjugated to an isotype; and a light-emitting nanoparticle which is not conjugated to neutravidin; and FIG. 10 is a staining index chart for Cyto-Trol cells stained with biotinylated nanoparticles having differing amounts of biotin according to embodiments of the present disclosure conjugated through streptavidin to anti-human CD4 antibody; and a comparative dissolved light-emitting polymer marker conjugated to the same antibody.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

FIG. 1 illustrates a particle 100 according to some embodiments of the present disclosure.

The light-emitting particle 100 has a core 101 comprising or consisting a light-emitting material. The core 101 may comprise a matrix material, optionally an inorganic matrix material, optionally an inorganic oxide, optionally silica.

If a matrix material is present then in some embodiments the light-emitting material may be covalently bound, directly or indirectly, to the matrix material. In some embodiments, the light-emitting material may be mixed with (i.e. not covalently bound to) a matrix material. The core 101 may comprise a silica shell partially or completely covering an inner core comprising or consisting of a light-emitting material, preferably a light-emitting polymer.

The core 101 may contain one or more light-emitting polymer chains mixed with and extending through the matrix material. One or more light-emitting polymer chains may protrude beyond a surface of the core defined by the matrix material.

Preferably, the particles have a number average diameter of no more than 5000 nm, more preferably no more than 2500 nm, 1000 nm, 900 nm, 800 nm, 700 nm, 600 nm, 500 nm or 400 nm as measured by dynamic light scattering (DLS) using a Malvern Zetasizer Nano ZS. Preferably the particles have a number average diameter of between 5-5000 nm, optionally 10-1000 nm, preferably between 10-500 nm, most preferably between 10-100 nm as measured by a Malvern Zetasizer Nano ZS.

In some embodiments, the light-emitting material is inorganic. Optionally, the inorganic light-emitting material is a quantum dot.

In some embodiments, the light-emitting material is organic. In some embodiments, the organic light-emitting material is non-polymeric. In some embodiments, the organic light-emitting material is a light-emitting polymer.

A first surface group 103 and a second surface group 105 are bound to the light-emitting particle core.

In some embodiments, the first surface group 103 and/or second surface group 105 may be covalently bound to a matrix material of the light-emitting particle core. The second surface group 105 comprises a biomolecule binding group 107. The first surface group 103 is inert, i.e. it does not comprise a biomolecule binding group.

The first surface group 103 comprises a first polar group PG1. The polar group may comprise heteroatoms capable of forming van der Waals bonds with water, optionally a linear or branched alkylene chain wherein one or more C atoms of the alkylene chain are replaced with O or $NR^6$ wherein $R^6$ is a $C_{1-12}$ hydrocarbyl group, optionally a $C_{1-12}$ alkyl group or $C_{1-4}$ alkyl group.

PG1 may be a linear or branched polar group.

Preferably, PG1 is a polyether chain. By "polyether chain" as used herein is meant a divalent chain comprising a plurality of ether groups.

Preferably, PG1 comprises or consists of a repeating unit of formula (I):

$$—((CR^{14}R^{15})_b O)_c— \qquad (I)$$

wherein $R^{14}$ and $R^{15}$ are each independently H or $C_{1-6}$ alkyl and b is at least 1, optionally 1-5, preferably 2, and c is at least 2, optionally 2-1,000, preferably 10-500, 10-200 or 10-100.

Most preferably, PG1 comprises a polyethyleneglycol chain.

The first polar group is bound at one end, directly or indirectly, to the particle core. A binding group may be provided between the polar group and the particle core to bind the polar group to the particle core.

The binding group may comprise a siloxane group bound to silica at the surface of the particle core and a binding group BG bound to the polar group.

Optionally the binding group BG comprises or consists of a group selected from esters, amides, urea, thiourea, Schiff bases, a primary amine (C—N) bond, a maleimide-thiol adduct or a triazole formed by the cycloaddion of an azide and an alkyne.

The first polar group PG1 is substituted at the other end (in the case of a divalent chain), or each other end (in the case of a branched, trivalent or higher chain) with an end group EG. Optionally, the end group is an acid group or a salt or ester thereof, optionally a carboxylic acid, sulfonic acid or phosphonic acid group or a salt or ester thereof.

The first surface group is inert. By "inert" is meant that the first surface group does not bind to a biomolecule when brought into contact with the biomolecule in water at 25° C.

Suitably, the first surface group does not bind to a protein (in particular the amine group of a protein), for example an antibody or other protein.

The first polar group may be polydisperse. The first polar group may have a Mn of at least 500, optionally at least 2,000.

The first surface group may have a multimodal weight distribution, optionally a bimodal weight distribution.

The second surface group comprises a biomolecule binding group 107 capable of binding to a biomolecule. Biomolecule binding groups include, without limitation, DNA, RNA, peptides, carbohydrates, antibodies, antigens, enzymes, proteins and hormones. A preferred biomolecule binding group is biotin.

In some embodiments, the biotin biomolecule binding group binds directly to a target analyte.

In some embodiments, the biotin biomolecule binding group is bound to a protein having a plurality of biotin binding sites, preferably streptavidin, neutravidin, avidin or a recombinant variant or derivative thereof. Preferably, the protein is not luminescent.

A biotinylated biomolecule having a second biotin group is bound to the same protein.

The biotinylated biomolecule may be selected according to the target analyte. The biotinylated biomolecule may comprise an antigen binding fragment, e.g. an antibody, which may be selected according to a target antigen.

The biomolecule binding group 107 may be bound to the particle core by a group 105. Group 105 may be a second polar group PG2. The second polar group may be the same as or different from the first polar group PG1 of the first surface group. Group 105 may be bound directly to the surface of the particle core or may be bound to a binding group BG, which may be the same as or different from, preferably the same as, the binding group BG of the first surface group.

In some embodiments, the first surface group has a weight average molecular weight in the range of 750-7,500 Daltons, optionally in the range of 1,000-3,000 Daltons.

FIG. 1 illustrates a particle having two different surface groups. In some embodiments, the particle may have three, four or more different surface groups.

Surface Group Formation FIG. 2 illustrates a process of forming light-emitting marker particles according to some embodiments of the present disclosure.

According to some embodiments, light-emitting marker particles having first and second surface groups may be formed from a light-emitting particle core 101 carrying a plurality of first reactive groups RG1.

Optionally the first reactive group RG1 is selected from:
  amine groups, optionally —$NR^8{}_2$ wherein $R^8$ in each occurrence is independently H or a substituent, preferably H or a $C_{1-5}$ alkyl, more preferably H; —COOH; —OH, —SH; an alkene; an alkyne; and an azide.

First reactive group RG1 may be attached, directly or indirectly, to the particle core by reacting a compound comprising the reactive group RG1 with the particle core.

Optionally, the particle core comprises silica and the compound comprising reactive group RG1 has formula (I):

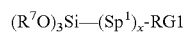

$$(R^7O)_3Si—(Sp^1)_x\text{-RG1} \qquad (I)$$

wherein $R^7$ is H or a substituent, preferably a $C_{1-10}$ alkyl group;

$Sp^1$ is a spacer group;

x is 0 or 1; and

RG1 is a first reactive group.

Preferably, a silane formed by reaction of the compound of formula (I) forms a monolayer on silica at the surface of the particle core.

Optionally, $Sp^1$ is selected from a linear or branched divalent alkylene chain wherein one or more non-adjacent C atoms may be replaced with O, S, C(=O), C(=O)O, C(=O)NR$^{12}$ or NR$^{12}$, wherein $R^{12}$ in each occurrence is independently selected from H and $C_{1-12}$ hydrocarbyl, optionally $C_{1-12}$ alkyl.

An exemplary compound of formula (I) is 3-aminopropyl triethoxysilane.

The particles are mixed with first and second reactive compounds. Some RG1 groups on the surface react with a first reactive compound 103' and some RG1 groups react with a second reactive compound 105' to form first and second surface groups respectively, or precursors thereof.

Each of the first and second reactive compounds comprise a second reactive group RG2 capable of reacting with reactive group RG1 to form a binding group BG, as described above, which covalently binds the first and second surface groups 103 and 105 to the particle core 101.

The molar ratio of first and second reactive compounds may be selected according to the desired first surface group:second surface group molar ratio. Second reactive group RG2 may be the same for the first and second reactive compounds or may be different.

Compound 103' may be a polydisperse compound. Compound 103' may have a multimodal, optionally bimodal, weight distribution. A multimodal weight distribution may be achieved by mixing polydisperse materials having different average molecular weights.

In some embodiments, compound 103' is formed by conversion of a precursor compound to form one or more second reactive groups RG2, such as by reaction of poly(ethylene glycol) to form at least one carboxylic acid group or ester thereof. A compound 103' having a multimodal weight distribution may be formed by mixing materials of different average molecular weights before or after formation of one or more reactive groups RG2.

In some embodiments, compound 103' comprises more than one second reactive group RG2. According to these embodiments, compound 103' may have formula (IIa):

In some embodiments, each RG2 group of formula (IIa) reacts with a reactive group RG1 to form a first surface group extending between two binding groups BG.

In some embodiments, only one RG2 group of formula (IIa) reacts with a reactive group RG1 to form a first surface group having reactive group RG2 as an end group. It will be understood that reactive group RG2 is selected for its reactivity with reactive group RG1; the reactive group RG2 may be selected from groups which do not bind to the target biomolecule.

RG1 and RG2 may be selected from:

amines, preferably —N(R$^8$)$_2$ wherein $R^8$ in each occurrence is H or a substituent, preferably H or a $C_{1-5}$ alkyl, more preferably H;

hydroxyl; thiol; and carboxylic acid or a derivative thereof which forms a carboxylic acid group or a salt thereof in the reaction between RG1 and RG2, for example an anhydride, acid chloride or ester.

Preferably, one of RG1 and RG2 is a carboxylic acid or a derivative thereof such as an ester, preferably an NHS ester, acid chloride or acid anhydride group and the other of RG1 and RG2 is a protic group such as a hydroxyl, thiol or amino group, preferably an amino group, wherein RG1 and RG2 are capable of reaction to form an ester or amide binding group BG. One of RG1 and RG2 may be converted to an activated form before reaction with RG2, for example activation of a carboxylic acid group using a carbodiimide, for example EDC.

In some embodiments, PG1 is a repeating unit of formula (I) which is bound directly to one or two reactive groups RG2, as described below.

In some embodiments, PG1 is a repeating unit of formula (I), PG1 further having a linking group linking the repeating unit of formula (I) to the or each reactive group RG2. Optionally, the linking group comprises or consists of an amide group.

Optionally, the compound of formula (IIa) has formula:

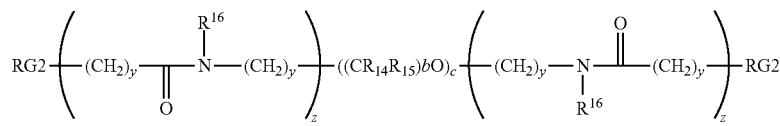

wherein RG2, $R^{14}$, $R^{15}$, b and c are as described above; each y is independently 0, 1, 2, 3, 4 or 5; each z is independently 0 or 1; and each $R^{16}$ is independently H or a $C_{1-6}$ alkyl group.

Second surface group 105 may comprise a polar group PG2, which may be selected from polar groups PG1 described above, and which may be the same as or different from polar group PG1 of the first surface group.

The biomolecule binding group 107 is preferably selected such that it does not react with RG1 under the reaction conditions for reacting RG1 and RG2, or such that RG2 preferentially reacts with RG1.

Preferably, the number of first surface groups 103 is greater than the number of second surface groups 105. Optionally, the number of moles of the first surface groups is at least 2 times, preferably 3 times, more preferably at least 5 times, the number of moles of the second surface groups. Most preferably, the number of second surface groups is less than 10 mol %, optionally up to 5 mol %, of the total number of moles of the first and second surface groups.

Preferably, the number of second surface groups is more than 0.1 mol %, optionally at least 0.5 mol %, of the total number of moles of the first and second surface groups.

Nanoparticle Core

The particle core may consist of one or more light-emitting materials.

The particle core may comprise or consist of one or more light-emitting materials and a matrix material. Matrix materials include, without limitation, inorganic matrix materials, optionally inorganic oxides, optionally silica.

In some embodiments, a silica particle is formed by the Stöber process, for example as described in WO 2018/060722, the contents of which are incorporated herein by reference.

In some embodiments, the particle core may be formed by polymerisation of a silica monomer in the presence of a light-emitting material, for example as described in WO 2018/060722, the contents of which are incorporated herein by reference.

Optionally, at least 0.1 wt % of total weight of the particle core consists of one or more light-emitting materials. Preferably at least 1, 10, 25 wt % of the total weight of the particle core consists of one or more light-emitting materials.

Optionally at least 50 wt % of the total weight of the particle core consists of the silica. Preferably at least 60, 70, 80, 90, 95, 98, 99, 99.5, 99.9 wt % of the total weight of the particle core consists of silica.

The particle core as described herein is the core without any surface binding groups or surface groups thereon.

In one embodiment of the present disclosure, at least 70 wt % of the total weight of the particle core consists of the light-emitting material or materials and silica. Preferably at least 80, 90, 95, 98, 99, 99.5, 99.9 wt % of the total weight of the particle core consists of the light-emitting material or materials and silica. More preferably the particle core consists essentially of the one or more light-emitting materials and silica.

Light-Emitting Materials

The light-emitting material of the particle core may emit fluorescent light, phosphorescent light or a combination thereof.

The light-emitting material may be a non-polymeric or polymeric light-emitting material. Polymeric light-emitting materials are preferred.

The light-emitting polymer may be a homopolymer or may be a copolymer comprising two or more different repeat units.

The light-emitting polymer may comprise light-emitting groups in the polymer backbone, pendant from the polymer backbone or as end groups of the polymer backbone. In the case of a phosphorescent polymer, a phosphorescent metal complex, preferably a phosphorescent iridium complex, may be provided in the polymer backbone, pendant from the polymer backbone or as an end group of the polymer backbone.

The light-emitting polymer may have a non-conjugated backbone or may be a conjugated polymer. By "conjugated polymer" is meant a polymer comprising repeat units in the polymer backbone that are directly conjugated to adjacent repeat units. Conjugated light-emitting polymers include, without limitation, polymers comprising one or more of arylene, heteroarylene and vinylene groups conjugated to one another along the polymer backbone.

The light-emitting polymer may have a linear, branched or crosslinked backbone.

The light-emitting polymer may comprise one or more repeat units in the backbone of the polymer substituted with one or more substituents selected from non-polar and polar substituents.

Preferably, the light-emitting polymer comprises at least one polar substituent. The one or more polar substituents may be the only substituents of said repeat units, or said repeat units may be further substituted with one or more non-polar substituents, optionally one or more $C_{1-40}$ hydrocarbyl groups. The repeat unit or repeat units substituted with one or more polar substituents may be the only repeat units of the polymer or the polymer may comprise one or more further co-repeat units wherein the or each co-repeat unit is unsubstituted or is substituted with non-polar substituents, optionally one or more $C_{1-40}$ hydrocarbyl substituents.

$C_{1-40}$ hydrocarbyl substituents as described herein include, without limitation, $C_{1-20}$ alkyl, unsubstituted phenyl and phenyl substituted with one or more $C_{1-20}$ alkyl groups.

As used herein a "polar substituent" may refer to a substituent, alone or in combination with one or more further polar substituents, which renders the light-emitting polymer with a solubility of at least 0.01 mg/ml in an alcoholic solvent, preferably at least 00.1, 1, 5 or 10 mg/ml. Optionally, solubility is in the range of 0.01-10 mg/ml. The solubility is measured at 25° C. Preferably, the alcoholic solvent is a $C_{1-10}$ alcohol, more preferably methanol.

Polar substituents are preferably substituents capable of forming hydrogen bonds or ionic groups.

In some embodiments, the light-emitting polymer comprises polar substituents of formula —O($R^3$O)$_t$—$R^4$ wherein $R^3$ in each occurrence is a $C_{1-10}$ alkylene group, optionally a $C_{1-5}$ alkylene group, wherein one or more non-adjacent, non-terminal C atoms of the alkylene group may be replaced with O, $R^4$ is H or $C_{1-5}$ alkyl, and t is at least 1, optionally 1-10. Preferably, t is at least 2. More preferably, t is 2 to 5. The value of t may be the same in all the polar groups of formula —O($R^3$O)$_t$—$R^4$. The value of t may differ between polar groups of the same polymer.

By "$C_{1-5}$ alkylene group" as used herein with respect to $R^3$ is meant a group of formula —(CH$_2$)$_f$— wherein f is from 1-5.

Preferably, the light-emitting polymer comprises polar substituents of formula —O(CH$_2$CH$_2$O)$_t$—$R^4$ wherein t is at least 1, optionally 1-10 and $R^4$ is a $C_{1-5}$ alkyl group, preferably methyl. Preferably, t is at least 2. More preferably, t is 2 to 5, most preferably q is 3.

In some embodiments, the light-emitting polymer comprises polar substituents of formula —N($R^5$)$_2$, wherein $R^5$ is H or $C_{1-12}$ hydrocarbyl. Preferably, each $R^5$ is a $C_{1-12}$ hydrocarbyl.

In some embodiments, the light-emitting polymer comprises polar substituents which are ionic groups which may be anionic, cationic or zwitterionic. Preferably the ionic group is an anionic group.

Exemplary anionic groups are —COO$^-$, a sulfonate group; hydroxide; sulfate; phosphate; phosphinate; or phosphonate.

An exemplary cationic group is —N($R^5$)$_3^+$ wherein $R^5$ in each occurrence is H or $C_{1-12}$ hydrocarbyl. Preferably, each $R^5$ is a $C_{1-12}$ hydrocarbyl.

A light-emitting polymer comprising cationic or anionic groups comprises counterions to balance the charge of these ionic groups.

An anionic or cationic group and counterion may have the same valency, with a counterion balancing the charge of each anionic or cationic group.

The anionic or cationic group may be monovalent or polyvalent. Preferably, the anionic and cationic groups are monovalent.

The light-emitting polymer may comprise a plurality of anionic or cationic polar substituents wherein the charge of two or more anionic or cationic groups is balanced by a single counterion. Optionally, the polar substituents comprise anionic or cationic groups comprising di- or trivalent counterions.

The counterion is optionally a cation, optionally a metal cation, optionally $Li^+$, $Na^+$, $K^+$, $Cs^+$, preferably $Cs^+$, or an organic cation, optionally ammonium, such as tetraalkylammonium, ethylmethyl imidazolium or pyridinium.

The counterion is optionally an anion, optionally a halide; a sulfonate group, optionally mesylate or tosylate; hydroxide; carboxylate; sulfate; phosphate; phosphinate; phosphonate; or borate.

In some embodiments, the light-emitting polymer comprises polar substituents selected from groups of formula —$O(R^3O)_t$—$R^4$, groups of formula —$N(R^5)_2$, groups of formula $OR^4$ and/or ionic groups. Preferably, the light-emitting polymer comprises polar substituents selected from groups of formula —$O(CH_2CH_2O)_tR^4$, groups of formula —$N(R^5)_2$, and/or anionic groups of formula —$COO^-$. Preferably, the polar substituents are selected from the group consisting of groups of formula —$O(R^3O)_t$—$R^4$, groups of formula —$N(R^5)_2$, and/or ionic groups. Preferably, the polar substituents are selected from the group consisting of polyethylene glycol (PEG) groups of formula —$O(CH_2CH_2O)_tR^4$, groups of formula —$N(R^5)_2$, and/or anionic groups of formula —$COO^-$. $R^3$, $R^4$, $R^5$, and t are as described above.

Optionally, the backbone of the light-emitting polymer is a conjugated polymer.

Optionally, the backbone of the conjugated light-emitting polymer comprises repeat units of formula (III):

wherein $Ar^1$ is an arylene group or heteroarylene group; Sp is a spacer group; m is 0 or 1; $R^1$ independently in each occurrence is a polar substituent; n is 1 if m is 0 and n is at least 1, optionally 1, 2, 3 or 4, if m is 1; $R^2$ independently in each occurrence is a non-polar substituent; p is 0 or a positive integer, optionally 1, 2, 3 or 4; q is 0 or a positive integer, optionally 1, 2, 3 or 4; and wherein Sp, $R^1$ and $R^2$ may independently in each occurrence be the same or different.

Preferably, m is 1 and n is 2-4, more preferably 4. Preferably p is 0.

$Ar^1$ of formula (III) is optionally a $C_{6-20}$ arylene group or a 5-20 membered heteroarylene group. $Ar^1$ is preferably a $C_{6-20}$ arylene group, optionally phenylene, fluorene, benzofluorene, phenanthrene, naphthalene or anthracene, more preferably fluorene or phenylene, most preferably fluorene.

Sp-($R^1$)n may be a branched group, optionally a dendritic group, substituted with polar groups, optionally —$NH_2$ or —OH groups, for example polyethyleneimine.

Preferably, Sp is selected from:
$C_{1-20}$ alkylene or phenylene-$C_{1-20}$ alkylene wherein one or more non-adjacent C atoms may be replace with O, S, N or C=O;
a $C_{6-20}$ arylene or 5-20 membered heteroarylene, more preferably phenylene, which, in addition to the one or more substituents $R^1$, may be unsubstituted or substituted with one or more non-polar substituents, optionally one or more $C_{1-20}$ alkyl groups.

"alkylene" as used herein means a branched or linear divalent alkyl chain.

"non-terminal C atom" of an alkyl group as used herein means a C atom other than the methyl group at the end of an n-alkyl group or the methyl groups at the ends of a branched alkyl chain.

More preferably, Sp is selected from:
$C_{1-20}$ alkylene wherein one or more non-adjacent C atoms may be replaced with O, S or CO; and
a $C_{6-20}$ arylene or a 5-20 membered heteroarylene, even more preferably phenylene, which may be unsubstituted or substituted with one or more non-polar substituents.

$R^1$ may be a polar substituent as described anywhere herein. Preferably, $R^1$ is:
a polyethylene glycol (PEG) group of formula —$O(CH_2CH_2O)_tR^4$ wherein t is at least 1, optionally 1-10 and $R^4$ is a $C_{1-5}$ alkyl group, preferably methyl;
a group of formula —$N(R^5)_2$, wherein $R^5$ is H or $C_{1-12}$ hydrocarbyl; or
an anionic group of formula —$COO^-$.

In the case where n is at least two, each $R^1$ may independently in each occurrence be the same or different. Preferably, each $R^1$ attached to a given Sp group is different.

In the case where p is a positive integer, optionally 1, 2, 3 or 4, the group $R^2$ may be selected from:
alkyl, optionally $C_{1-20}$ alkyl; and
aryl and heteroaryl groups that may be unsubstituted or substituted with one or more substituents, preferably phenyl substituted with one or more $C_{1-20}$ alkyl groups;
a linear or branched chain of aryl or heteroaryl groups, each of which groups may independently be substituted, for example a group of formula —$(Ar^3)_s$ wherein each $Ar^3$ is independently an aryl or heteroaryl group and s is at least 2, preferably a branched or linear chain of phenyl groups each of which may be unsubstituted or substituted with one or more $C_{1-20}$ alkyl groups; and
a crosslinkable-group, for example a group comprising a double bond such and a vinyl or acrylate group, or a benzocyclobutane group.

Preferably, each $R^2$, where present, is independently selected from $C_{1-40}$ hydrocarbyl, and is more preferably selected from $C_{1-20}$ alkyl; unsubstituted phenyl; phenyl substituted with one or more $C_{1-20}$ alkyl groups; and a linear or branched chain of phenyl groups, wherein each phenyl may be unsubstituted or substituted with one or more substituents.

A polymer as described herein may comprise or consist of only one form of the repeating unit of formula (III) or may comprise or consist of two or more different repeat units of formula (III).

Optionally, the polymer comprising one or more repeat units of formula (III) is a copolymer comprising one or more co-repeat units.

If co-repeat units are present then the repeat units of formula (III) may form between 0.1-99 mol % of the repeat units of the polymer, optionally 50-99 mol % or 80-99 mol %. Preferably, the repeat units of formula (I) form at least 50 mol % of the repeat units of the polymer, more preferably at least 60, 70, 80, 90, 95, 98 or 99 mol %. Most preferably the repeat units of the polymer consist of one or more repeat units of formula (I).

The or each repeat unit of the polymer may be selected to produce a desired colour of emission of the polymer.

The light-emitting material may emit light having a peak wavelength in the range of 350-1000 nm.

A blue light-emitting material, e.g. a blue light-emitting polymer of a composite particle as described herein may have a photoluminescence spectrum with a peak of no more than 500 nm, preferably in the range of 400-500 nm, optionally 400-490 nm.

A green light-emitting material, e.g. a green light-emitting polymer of a composite particle as described herein may have a photoluminescence spectrum with a peak of more than 500 nm up to 580 nm, optionally more than 500 nm up to 540 nm.

A red light-emitting material, e.g. a red light-emitting polymer of a composite particle as described herein may have a photoluminescence spectrum with a peak of no more than more than 580 nm up to 630 nm, optionally 585 nm up to 625 nm.

The light-emitting material may have an absorption spectrum having a maximum in the range of 300-900 nm.

The light-emitting material may have a Stokes shift in the range of 10-850 nm.

The photoluminescence spectrum of a light-emitting polymer as described herein may be measured in solution using apparatus C9920-02 supplied by Hamamatsu.

UV/vis absorption spectra of light-emitting materials as described herein may be as measured in solution or suspension using a Cary 5000 UV-vis-IR spectrometer.

Arylene repeat units of the polymer include, without limitation, fluorene, preferably a 2,7-linked fluorene; phenylene, preferably a 1,4-linked phenylene; naphthalene, anthracene, indenofluorene, phenanthrene and dihydrophenanthrene repeat units.

The polystyrene-equivalent number-average molecular weight (Mn) measured by gel permeation chromatography of the light-emitting polymers or the silica polymers described herein may be in the range of about $1\times10^3$ to $1\times10^8$, and preferably $1\times10^4$ to $5\times10^6$. The polystyrene-equivalent weight-average molecular weight (Mw) of the polymers described herein may be $1\times10^3$ to $1\times10^8$, and preferably $1\times10^4$ to $1\times10^7$.

Polymers as described herein are suitably amorphous polymers.

Colloids

The particles may be provided as a colloidal suspension comprising the particles suspended in a liquid. Preferably, the liquid is selected from water, $C_{1-10}$ alcohols and mixtures thereof. Preferably, the particles form a uniform (non-aggregated) colloid in the liquid.

The liquid may be a solution comprising salts dissolved therein, optionally a buffer solution. The buffer solution may have a pH in the range of 1-14, preferably 5-8. The buffer solution may contain without limitation, a phosphate e.g. sodium phosphate, tris(hydroxymethyl)aminomethane (tris), an acetate e.g. sodium acetate, a borate, and/or 2-(A-morpholino)ethanesulfonic acid (MES).

The salt concentration of a buffer solution may be in the range of about 1 mmol/L-200 mmol/L.

The concentration of the particles in the colloidal suspension is preferably in the range of 0.1-20 mg/mL, optionally 5-20 mg/mL.

In some embodiments, the particles may be stored as a colloidal suspension, optionally a colloidal suspension having a particle concentration greater than 0.1 mg/mL, preferably at least 0.5 mg/mL or 1 mg/mL.

In some embodiments, the particles may be stored in a lyophilised or frozen form.

Applications

The particles of the present disclosure may be fluorescent or phosphorescent. Preferably the particles are fluorescent. Preferably the particles are for use as a fluorescent probe for detecting a biomolecule or for labelling a biomolecule. In some embodiments, the particles may be used as a fluorescent probe in an immunoassay such as a lateral flow or solid state immunoassay. Optionally the particles are for use in fluorescence microscopy, flow cytometry, next generation sequencing, in-vivo imaging, or any other application where a light-emitting marker configured to bind to a target analyte is brought into contact with a sample to be analysed. The applications can medical, veterinary, agricultural or environmental applications whether involving patients (where applicable) or for research purposes.

In use the biomolecule binding group of the particles may bind to target biomolecules which include without limitation DNA, RNA, peptides, carbohydrates, antibodies, antigens, enzymes, proteins and hormones. It will be understood that the biomolecule binding group may be selected according to the target biomolecule.

A sample to be analysed may brought into contact with the particles, for example the particles in a colloidal suspension.

In some embodiments, the sample following contact with the particles is analysed by flow cytometry. In flow cytometry, the particles are irradiated by at least one wavelength of light, optionally two or more different wavelengths, e.g. one or more wavelengths including at least one of 355, 405, 488, 562 and 640 nm. Light emitted by the particles may be collected by one or more detectors. Detectors may be selected from, without limitation, photomultiplier tubes and photodiodes. To provide a background signal for calculation of a staining index, measurement may be made of particles mixed with cells which do not bind to the particles.

In some embodiments, e.g. a plate assay, the target biomolecule may be immobilised on a surface which is brought into contact with the particles.

Example 1—Biotinylated Nanoparticle Formation

Formation of Light-Emitting Nanoparticle Cores with Reactive Amine Groups

Nanoparticles having a core of silica and a light-emitting polymer were formed by the Stöber process and the nanoparticle cores were reacted with (3-aminopropyl)triethoxysilane as described in the examples of WO 2018/060722, the contents of which are incorporated herein by reference, to give nanoparticles with a number average diameter by dynamic light scattering of 80 nm and amine reactive groups on the surface of the cores.

Attachment of Surface Groups to Amino-Modified Light-Emitting Nanoparticles 1 mL of the suspension of amino-modified nanoparticle cores in methanol formed in the example above was centrifuged at 14,000 rpm for 2 minutes to isolate the nanoparticles through decantation of the supernatant. A 1 mL solution of α,ω-Bis{2-[(3-carboxy-1-oxopropyl)amino]ethyl}(polyethylene glycol (SAA-PEG-SAA, illustrated below, MW=2000 g/mol), biotin-PEG-COOH (MW=2000 g/mol), N-(3-aminopropyl)-N-ethylcarbodiimide (2.1 mg) and N-hydroxysuccinimide (2.5 mg) in methanol was used to redisperse the nanoparticle pellet by gentle sonication and the resultant suspension was stirred at room temperature for 1 hour. Relative amounts of the SAA-PEG-SAA and biotin-PEG-COOH are shown in Table 1. The suspension was centrifuged at 14,000 rpm for 2 minutes to isolate the resultant silica-LEP nanoparticles from the supernatant containing excess unreacted PEGylation reagents. The supernatant was removed by decantation and gentle sonication was used to redisperse the isolated pellet of nanoparticles in 1 mL of fresh methanol. Wash cycles consisting of centrifugation, decantation and redispersion in methanol (1 mL) were repeated a further two times.

Before the final centrifugation and decantation, the suspension was aliquoted into four 250 μL portions and the resultant pellets were stored at −20° C. prior to use.

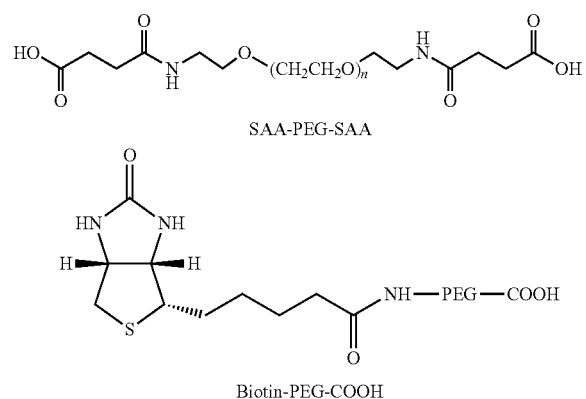

SAA-PEG-SAA

Biotin-PEG-COOH

TABLE 1

| Sample | Mass of SAA-PEG-SAA | Mass of biotin-PEG-COOH |
| --- | --- | --- |
| 0.1 wt % biotin | 9.99 mg | 0.01 mg |
| 1 wt % biotin | 9.9 mg | 0.1 mg |
| 10 wt % biotin | 9 mg | 1 mg |

Example 2—Conjugation of Biotinylated Nanoparticles to Streptavidin

One of the isolated PEGylated nanoparticle pellets of Example 1 was resuspended in 1 mL of phosphate buffered saline (pH 7.4, containing 1 wt. % bovine serum albumin) by gentle sonication, followed by immediate addition of 50 μL of a solution of streptavidin in the same buffer (1 mg/mL). The suspension was stirred at room temperature for 1 hour before centrifuging the sample at 14000 rpm for 3 minutes to collect separate the protein-conjugated nanoparticles from the supernatant and unconjugated protein. The pellet was resuspended by gentle sonication in 100 μL of phosphate buffered saline for storage.

Example 3—Stability of Nanoparticles

A colloid of nanoparticles carrying inert PEG surface groups and biotin-substituted PEG surface groups as described in Example 1 was formed with phosphate buffered saline (PBS, pH 7.4) and the Z average diameter of the nanoparticles was measured periodically using dynamic light scattering to determine aggregation of the nanoparticles.

With reference to Table 1, aggregation is surprisingly reduced at higher nanoparticle concentrations, in particular concentrations above 0.1 mg/mL.

The stabilities in PBS of nanoparticles described in Examples 1 and 2 (i.e. with and without streptavidin), with 1 mol % or 10 mol % of biotin-substituted PEG groups, was studied.

With reference to Table 2, stability is much higher in lower concentration PBS for both 1 mol % and 10 mol % biotin-substituted PEG groups without streptavidin. Stability is considerably lower upon attachment of streptavidin at the higher concentration of biotin-substituted PEG groups. However, both of these nanoparticles were found to be much more stable than a nanoparticle for which 100% of the surface groups carry biotin substituted PEG groups; this nanoparticle was found to undergo aggregation within minutes of dispersal in PBS.

TABLE 2

| Surface groups carrying biotin | Biomolecule bound to biotin | Stability of 1 mg/mL nanoparticles in 10 mM PBS (hours) | Stability of 0.1 mg/mL nanoparticles in 0.1 mM PBS (hours) |
| --- | --- | --- | --- |
| 10% | None | >336 | ~24 |
|  | Streptavidin | <0.25 | <0.25 |
| 1% | None | >336 | ~24 |
|  | Streptavidin | Partial aggregation after ~168 hours, reversible by sonication | ~24 |

The stability time of Table 2 is the time taken for Z-average diameter of the particles as determined by dynamic light scattering to exceed 10% of a starting diameter upon storage at 5° C. and without agitation between measurements.

The possibility of streptavidin causing aggregation by binding to biotin molecules of different nanoparticles was investigated by using streptavidin-containing particles formed using the process of Example 2 with a large excess of streptavidin to reduce or eliminate the occurrence of nanoparticles with free biotin groups. Similar aggregation was observed, indicating that streptavidin was not facilitating aggregation by binding to different nanoparticles.

Example 4—Effect of Aggregation on Bio-Assay Sensitivity

Preparing Biotin-BSA Modified Glass Slides for Bio-Assay

A glass microscope slide functionalised with a self-assembled monolayer of (3-aminopropyl)silane was submersed in a solution containing succinic anhydride (1 g) and trimethylamine (1.3 mL) in acetonitrile (50 mL) for 16 hours, before washing three times with fresh acetonitrile (50 mL). After drying, a Grace-Biolabs Secure Seal imaging spacer was affixed to the surface of the resultant carboxy-functionalised glass slide in order to isolate four circular areas (diameter=9 mm) for use in the subsequent binding assay. Within each isolated area of the slide was added 80 μL of a 1 mL solution containing N-(3-aminopropyl)-N-ethyl-carbodiimide (77.0 mg) and N-hydroxysulfosuccinimide (33.0 mg). After leaving at room temperature for 30 mins, the solutions were removed and isolated areas washed three times with water (80 μL). After removing the last wash solution, to two of the areas was added 80 μL of a solution of biotinylated bovine serum albumin (50 μg/mL) in phosphate buffered saline (pH 7.4) and to the two remaining areas was added 80 μL of a blocking buffer containing bovine serum albumin (3 wt. %) in phosphate buffered saline (pH 7.4) containing 0.01 wt. % Tween-20. After 1 hour at room temperature, solutions were removed from the two areas containing biotinylated bovine serum albumin solutions and in their place was added 80 μL of the blocking buffer described above. After a further hour at room temperature, solutions were removed from all four areas and each was washed three times with phosphate buffered saline (pH 7.4) containing 0.01 wt. % Tween-20.

Biotin-Binding Assay Using Streptavidin-Modified Nanoparticles

Colloids containing 0.1 mol %, 1 mol % and 10 mol % of streptavidin-modified biotinylated nanoparticles described in Example 2 (0.1 mg/mL in phosphate buffered saline containing 1% bovine serum albumin) were applied to the glass slide. After leaving for 30 min at room temperature, the solution was removed and washed three times with 80 µL of phosphate buffered saline (pH 7.4). After allowing to dry in air, the fluorescence intensity of each of the four assay regions was measured using a microscope-based spectrometer, using a mercury lamp as the excitation source (λex=365 nm) and a fibre-optic spectrometer for detection. The signal-noise was determined by dividing the averaged integrated intensity from the areas functionalised with biotin by the averaged intensity of the areas blocked with just BSA (no biotin).

As shown in FIG. 3, the strongest signal-to-noise ratio was observed for the 1 mol % biotinylated nanoparticles. Without wishing to be bound by any theory, this is attributed to a higher percentage of biotinylated groups compared to the 0.1 mol % biotinylated nanoparticles and less aggregation (which may make the binding groups less accessible) compared to the 10 mol % biotinylated nanoparticles.

Example 5—Effect of Surface Group Molecular Weight

Nanoparticles were prepared as described for Example 1, except that the amino groups were reacted with SAA-PEG-SAA only (Mw 550, 100, 2000 or 5000 Da) or with mPEG-SAA only (illustrated below, MW 550, 100, 2000 and 5000 Da), i.e. the resultant surface groups did not include groups having a biomolecule binding group.

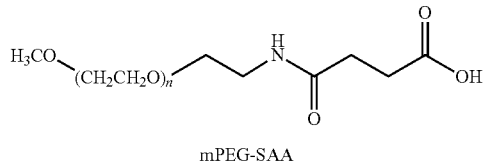

mPEG-SAA

All particles were found to form dispersions in methanol which remained stable for more than 1 month.

To determine stability of the particles in a buffered solution, a 1 mg/mL dispersion of the PEG coated particles in methanol was measured by DLS to determine the Z-average diameter of the particles.

1 mg of nanoparticles was then isolated from the methanol dispersant by centrifugation and decantation of the supernatant and was redispersed in 1 mL phosphate buffered saline (PBS, pH 7.4) by sonicating in an ultrasonic bath for 5 minutes.

DLS measurements of the dispersion in PBS were measured after 5, 60, 300 and 1440 min (or until such time as they aggregated), leaving the sample to stand at room temperature in a sealed sample tube between measurements.

With reference to FIG. 4, all nanoparticles having methoxy PEG terminated surface groups formed by reaction of the core with mPEG-SAA were found to have aggregated within 5 minutes of dispersal in PBS.

With reference to FIG. 5, nanoparticles having carboxy-terminated surface groups formed by reaction of the core with SAA-PEG-SAA were stable for up to 24 hours dependent on Mw of the surface group.

Example 6—conjugation to a biotinylated antibody to 1 mg of the streptavidin-functionalised nanoparticles described in Example 2, 250 µL of 0.5 mg/mL biotinylated goat anti-mouse antibody (clone Poly4053, purchased from Biolegend) was added, and the mixture was agitated for 1 h at room temperature. This step was repeated four times; on the final step the pellet was resuspended in 500 µL BSA/PBS to give a final particle concentration of 2 mg/mL.

Example 7—Flow Cytometry Assays

Flow cytometry analysis was carried out on a Propel Labs YETI analyser.

BV421-anti-human CD4 (clone SK3) [BV421-hCD4] and BV421-mouse IgG1, κ isotype (clone MOPC-21) [BV421-isotype] were purchased from Biolegend.

CYTO-TROL cells were supplied by Beckman Coulter.

1. CYTO-TROL cells were brought up to room temperature and resuspended in the buffer supplied by the manufacturer before use.
2. Antibody-tag dilutions were made to the required concentrations in BSA/PBS in microcentrifuge tubes.
3. 100 µL of prepared Cyto-Trols were added to each of the antibody-NP dilutions. The preparations were mixed well and left to incubate at 4° C. for 30 minutes, avoiding direct light.
4. After incubation, the cells were washed twice with cell staining buffer, centrifuged at 2000 rpm for 3 minutes at 4° C., and the supernatant was discarded.
5. The cells were resuspended in 200 µL cell staining buffer ready for analysis.
6. For analysis, a flow rate of 0.5 µL/sec was used. Data was gated on single cells, and 10,000 events were acquired in this gate for each measurement.

A series of different exemplary nanoparticles NP(x)-hCD4 (where NP is a nanoparticle as described in Example 6, x=s for streptavidin; x=n for neutravidin; hCD4=anti-human CD4 antibody) dilutions were screened to determine the optimal working concentration for maximum staining index of each dye.

Conjugation of antibodies using neutravidin is as described above for streptavidin except that 50 µL of a 1 mg/mL solution of neutravidin in PBS was used in place of streptavidin.

Staining index [SI] is:

$$SI=(MFI1-MFI2)/2\times SD)$$

where MFI1 is the median fluorescence intensity of the positive population; MFI2 is the median fluorescence intensity of the negative population, and SD is the standard deviation of the negative signal.

The same was done for comparative marker BV421-hCD4 wherein BV421 is the dissolved fluorescent polymer Brilliant Violet 421™ available from BioLegend.

Voltages were adjusted to ensure both negative and positive signals were on scale. For NP(n)-hCD4 it was not possible to find a voltage where negatives and positives were fully on scale, so voltages where the negatives were fully on scale were used for analysis.

TABLE 1

| | Tag | |
|---|---|---|
| | BV421-hCD4 | NP(x)-hCD4 |
| Concentrations screened (µg/mL) | 500 | 125 |
| | 250 | 62.5 |
| | 125 | 31.3 |
| | 62 | 15.6 |
| | 31 | 7.8 |

Optimal concentrations for each tag were determined as:

BV421-hCD4: 250 µg/mL

NP(s)-hCD4: 31.3 µg/mL

NP(n)-hCD4: 15.6 µg/mL

The optimal voltages for BV421-hCD4, NP(s)-hCD4 and NP(n)-hCD4 for each channel were the same, and are summarised in Table 2:

TABLE 2

| Emission Channel (Laser line nm) | Voltage/V |
|---|---|
| FSC | 370 |
| SSC | 478 |
| 420/10 (405) | 470 |
| 460/22 (405) | 421 |
| 525/50 (405) | 380 |
| 615/24 (405) | 471 |
| 525/35 (488) | 460 |
| 593/52 (488) | 424 |
| 692/80 (488) | 520 |
| 750LP (488) | 630 |

Each of the following tags of Table 3 were measured in triplicate at their optimum concentration and optimised voltages as described above:

TABLE 3

| Tag type | Tag | Controls |
|---|---|---|
| BV421 | BV421-hCD4 | BV421-isotype |
| NP(s) | NP(s)-hCD4 | NP(s)-isotype |
| NP(n) | NP(n)-hCD4 | NP(n)-isotype |

The same was done for the biotinylated nanoparticle of Example 1 (i.e. without streptavidin or neutravidin) and unstained cells.

These particles not conjugated to streptavidin or neutravidin were aliquoted into a microcentrifuge tube. The suspension was centrifuged at 14,000 rpm for 4 min; the solvent decanted and the pellet resuspended in 100 µL of BSA/PBS with ultrasonication to give a final particle concentration of 10 mg/mL.

Results; NP(s)-hCD4

The staining of Cyto-Trol cells with NP(s)-hCD4 is compared with BV421-hCD4 in FIG. 6 and Table 4. Similar to BV421-hCD4, NP(s)-hCD4 shows negligible staining of negative cells. The positive signal for NP(s)-hCD4 however is significantly shifted to higher extinction coefficients, with only a slight increase in the standard deviation of the positive signal relative to BV421-hCD4. This increase in MFI1 leads to a ~2.5× increase in staining index for NP(s)-hCD4 relative to BV421.

TABLE 4

| Tag | Brightness (MFI1-MFI2) | Background (2 × SD) | Staining Index |
|---|---|---|---|
| NP(s)-hCD4 | 17874 | 57 | 314 |
| BV421-hCD4 | 4834 | 38 | 127 |

The low negative staining of NP(s)-derived particles are further demonstrated in FIG. 7 and Table 5. Neither the unfunctionalised, NP(s)-isotype or the NP(s)-hCD4 show any significant negative staining, showing that fluorescent nanoparticles and their streptavidin- and antibody-conjugated derivatives as described herein have low non-specific absorption to cells.

TABLE 5

| Experiment | Background (2 × SD) |
|---|---|
| Negative | 35 |
| NP(no protein) | 57 |
| NP(s)-isotype | 48 |
| NP(s)-hCD4 | 57 |

Results; NP(n)-hCD4

As for NP(s)-hCD4, the staining of Cyto-Trol cells with NP(n)-hCD4 is compared with BV421-hCD4 in FIG. 8 and Table 6. As with NP(s)-hCD4, NP(n)-hCD4 shows negligible negative staining. The brighter positive signal for NP(n)-hCD4 gives a staining index of 5.4× relative to BV421-hCD4.

TABLE 6

| Tag | Brightness (MFI1-MFI2) | Background (2 × SD) | Staining Index |
|---|---|---|---|
| NP(n)-hCD4 | 29376 | 43 | 681 |
| BV421-hCD4 | 4834 | 38 | 127 |

The low negative staining of NP(n)-derived particles are further demonstrated in FIG. 9 and Table 7. Neither the unfunctionalised, NP(n)-isotype or the NP(n)-hCD4 show any significant negative staining, showing that fluorescent NPs and their neutravidin- and antibody-conjugated derivatives have low non-specific absorption to cells.

TABLE 7

| Experiment | Background (2 × SD) |
|---|---|
| Negative | 35 |
| NP(no protein) | 57 |
| NP(n)-isotype | 32 |
| NP(n)-hCD4 | 43 |

Effect of First Biotin Group Density

The effect of the first biotin group density (and therefore the number of protein binding sites on the surface of the precursor nanoparticle) was studied using nanoparticles as described in Example 1 except that biotin-PEG-COOH as a percentage of the total weight of biotin-PEG-COOH+SAA-PEG-SAA was varied to 0.5 wt %, 1 wt %, 5 wt % and 10 wt %.

Volumes of reagents used for different weight percentages of the first and second surface groups are shown in Table 8:

TABLE 8

| Wt % Biotin | (A) Nanoparticle volume for streptavidin conj./μL | (B) Volume of streptavidin/μL | (C) Nanoparticle volume for IgG conj./μL | (D) Biotinylated antibody volume/μL |
|---|---|---|---|---|
| 0.5 | 731 | 18.8 | 656 | 93.7 |
| 1 | 713 | 37.5 | 563 | 188 |
| 5 | 563 | 188 | 506 | 244 |
| 10 | 375 | 375 | 255 | 495 |

Nanoparticles conjugated to anti-human CD4 [NP(x)-hCD4] were formed using biotin mouse anti-human CD4 antibody (clone SK3) supplied by Biolegend.

Isotype control particles [NP(x)-isotype] used biotin mouse IgG1, κ isotype (clone MOPC-21) supplied by Biolegend.

A series of different NP(s)-x % hCD4 (where x=0.5, 1, 5 or 10, representing the percentage PEG-biotin used to functionalise the NP) and BV421-hCD4 dilutions were screened to determine the optimal working concentration for maximum staining index of each dye.

Voltages were adjusted to ensure both negative and positive signals were on scale.

TABLE 9

| | Tag | |
|---|---|---|
| | BV421-hCD4 | NP(s)-x % hCD4 |
| Concentrations screened (μg/mL) | 500 | 500 |
| | 250 | 250 |
| | 125 | 125 |
| | 62 | 62 |
| | 31 | 31 |

Optimal concentrations for each tag were determined as:

BV421-hCD4: 250 μg/mL

NP(s)-0.5% hCD4: 62.5 μg/mL

NP(s)-1% hCD4: 250 μg/mL

NP(s)-5% hCD4: 125 μg/mL

NP(s)-10% hCD4: 62.5 μg/mL

The optimal voltages for BV421-hCD4 and NP(s)-x % hCD4 for each channel were the same, and are summarised in Table 10:

TABLE 10

| Emission Channel (Laser line) | Voltage/V |
|---|---|
| FSC | 370 |
| SSC | 478 |
| 420/10 (405) | 470 |
| 460/22 (405) | 421 |
| 525/50 (405) | 380 |
| 615/24 (405) | 471 |
| 525/35 (488) | 460 |
| 593/52 (488) | 424 |
| 692/80 (488) | 520 |
| 750LP (488) | 630 |

Tags of Table 11 were measured in triplicate at their optimum concentration and optimised voltages as described above:

TABLE 11

| Tag type | Tag | Controls |
|---|---|---|
| BV421 | BV421-hCD4 | BV421-isotype |
| NP(s)-0.5% | NP(s)-0.5% hCD4 | NP(s)-0.5% isotype |
| NP(s)-1% | NP(s)-1% hCD4 | NP(s)-1% isotype |
| NP(s)-5% | NP(s)-5% hCD4 | NP(s)-5% isotype |
| NP(s)-10% | NP(s)-10% hCD4 | NP(s)-10% isotype |

Unstained cells were also measured.

The effect of changing the percentage of surface biotin groups on the staining of Cyto-Trol cells is illustrated in FIG. 10 and Table 12. For all biotin concentrations, the negative population showed negligible background staining relative to unstained cells, with the exception of 1% biotin, which is attributed to the very high optimal staining concentration (250 μg/mL) compared to the other tags. The effect of this high staining concentration is apparent from the NP(s)-1% hCD4 used in the streptavidin/neutravidin comparison experiments above which show negligible staining for the negative population at the much lower optimal staining concentration of 31.3 μg/mL.

Therefore, it can be concluded that variation of the surface biotin concentration between 100.5-10% does not increase the non-specific binding of the resulting tag to Cyto-Trol cells.

TABLE 12

| Tag | Brightness (MFI1-MFI2) | Background (2 × SD) | Staining Index |
|---|---|---|---|
| BV421-hCD4 | 4731 | 50 | 107 |
| NP(s)-0.5% hCD4 | 7254 | 57 | 127 |
| NP(s)-1% hCD4 | 16043 | 110 | 146 |
| NP(s)-5% hCD4 | 21908 | 96 | 229 |
| NP(s)-10% hCD4 | 21517 | 90 | 240 |

These data demonstrate that more surface biotin results in a higher staining index of the resulting antibody conjugate, with 10 wt % biotin tags showing a 1.9× higher staining index than 0.5 wt % biotin tags. Even at 0.5 wt % biotin, the staining index exceeds that of BV421-hCD4.

The invention claimed is:

1. A light-emitting marker particle comprising a light-emitting particle core, first surface groups bound to the light-emitting particle core and second surface groups bound to the light-emitting particle core, wherein: the light-emitting particle core comprises a light-emitting polymer; the first surface group comprises a polar group; the first surface group is inert; the second surface group comprises a biomolecule binding group; and a number of moles of the second surface group is less than 10% of a total number of moles of the first and second surface groups.

2. The light-emitting marker particle according to claim 1 wherein the polar group comprises a polyether chain.

3. The light-emitting marker particle according to claim 2 wherein the polar group is a group of formula (I):

$$-((CR^{14}R^{15})_b O)_c- \qquad (I)$$

wherein $R^{14}$ and $R^{15}$ are each independently H or $C_{1-6}$ alkyl; b is at least 1; and c is at least 2.

4. The light-emitting marker particle according to claim 1 wherein the biomolecule binding group is selected from the group consisting of: DNA, RNA, peptides, carbohydrates, antibodies, antigens, enzymes, proteins and hormones.

5. The light-emitting marker particle according to claim 1 wherein the second surface group comprises a polar group between the light-emitting particle core and the biomolecule binding group.

6. The light-emitting marker particle according to claim 1 wherein the light-emitting particle core comprises an inorganic matrix.

7. The light-emitting marker particle according to claim 6 wherein the inorganic matrix is an inorganic oxide.

8. The light-emitting marker particle according to claim 7 wherein the inorganic oxide is silica.

9. A method of forming a light-emitting marker particle according to claim 1 comprising:
providing a light-emitting particle core having a plurality of a first reactive group bound to a surface thereof;
forming the first surface group, wherein formation of the first surface group comprises reacting a portion of the first reactive groups with a first compound; and
forming the second surface group, wherein formation of the second surface group comprises reacting a portion of the first reactive groups with a second compound.

10. A method according to claim 9 wherein the first reactive groups react with at least one of the first and second compounds to form amide binding groups binding the first or second surface groups to the light-emitting particle core.

11. A method according to claim 9 wherein the first reactive group is formed on the surface thereof by reacting a compound of formula (I) with silica at the surface of the light-emitting particle core:

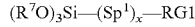
(I)

wherein $R^7$ is H or a substituent;
$Sp^1$ is a spacer group;
x is 0 or 1; and
RG1 is the first reactive group.

12. A colloid comprising light-emitting marker particles according to claim 1 suspended in a liquid.

13. A colloid according to claim 12 wherein the liquid comprises water.

14. A colloid according to claim 12 wherein the liquid is a buffer solution.

15. A colloid according to claim 12 wherein a concentration of the light-emitting marker particles is more than 0.1 mg/mL.

16. A method of marking a biomolecule, the method comprising the step of binding the biomolecule to a light-emitting marker particle according to claim 1.

17. An assay method for a target analyte comprising contacting a sample with light-emitting marker particles according to claim 1 and determining any binding of the target analyte to the light-emitting marker.

18. An assay method according to claim 17 wherein the sample contacted with the light-emitting marker particles is analysed by flow cytometry.

19. The light-emitting marker particle according to claim 2, wherein b is 1-5; and c is 2-1,000.

20. The light-emitting marker particle according to claim 2, wherein b is 2; and c is 10-500, 10-200, 10-100, or 20-50.

* * * * *